(12) United States Patent
Kottayil et al.

(10) Patent No.: US 11,857,520 B2
(45) Date of Patent: Jan. 2, 2024

(54) THERAPEUTIC COMPOSITION OF INTRANASAL LIDOCAINE

(71) Applicant: Nortic Holdings Inc., East Brunswick, NJ (US)

(72) Inventors: S. George Kottayil, West Windsor, NJ (US); Amresh Kumar, Plainsboro, NJ (US); Prasanna Sunthankar, West Windsor, NJ (US); Vimal Kavuru, Holmdel, NJ (US); Kamalkishore Pati, Old Bridge, NJ (US)

(73) Assignee: Nortic Holdings Inc.

( * ) Notice: Subject to any disclaimer, the term of this patent is extended or adjusted under 35 U.S.C. 154(b) by 606 days.

(21) Appl. No.: 16/703,444

(22) Filed: Dec. 4, 2019

(65) Prior Publication Data

US 2020/0197338 A1 Jun. 25, 2020

Related U.S. Application Data

(60) Provisional application No. 62/781,969, filed on Dec. 19, 2018.

(51) Int. Cl.
| | | |
|---|---|---|
| *A61K 31/167* | (2006.01) | |
| *A61M 11/00* | (2006.01) | |
| *A61K 9/00* | (2006.01) | |

(52) U.S. Cl.
CPC .......... *A61K 31/167* (2013.01); *A61K 9/0043* (2013.01); *A61M 11/00* (2013.01); *A61M 2210/0618* (2013.01)

(58) Field of Classification Search
CPC ..... A61K 31/167; A61K 9/0043; A61P 25/04; A61P 25/06
See application file for complete search history.

(56) References Cited

U.S. PATENT DOCUMENTS

| 5,008,289 A | 4/1991 | Bernstein |
| 2001/0055607 A1 | 12/2001 | Levin |
| 2009/0312724 A1 * | 12/2009 | Pipkin .................. A61K 31/724 |
| | | 128/207.18 |
| 2011/0023870 A1 | 2/2011 | Wermeling |
| 2011/0118189 A1 | 5/2011 | Farr et al. |
| 2012/0149643 A1 * | 6/2012 | Fein ...................... A61M 15/08 |
| | | 514/10.9 |

FOREIGN PATENT DOCUMENTS

| WO | WO 00/44432 | 8/2000 | |
| WO | WO-2009152369 A1 * | 12/2009 | ........... A61K 31/167 |

OTHER PUBLICATIONS

International Search Report and Written Opinion from corresponding International PCT Application No. PCT/US2019/064472 dated Feb. 7, 2020.
Marx et al. "Multi-Dose Container for Nasal and Ophthalmic Drugs: A preservative Free Future?" Aptar Pharma, Consumer Healthcare Division, Germany; Retrieved from the internet <URL: https://pharma.aptar.com/sites/default/files/publications/intech_bookchapter.pdf>; pp. 519-520 (Dec. 7, 2011).
Extended European Search Report from corresponding European Application No. 19 90 0739 dated Aug. 17, 2022.
P. Bowen, "Particle Distribution Measurement from Millimeters to Nanometers and from Rods to Platelets", Journal of Dispersion Science and Technology, vol. 23, No. 5, pp. 631-662, 2002.

* cited by examiner

*Primary Examiner* — Michael B. Pallay
(74) *Attorney, Agent, or Firm* — Davidson, Davidson & Kappel, LLC (57) ABSTRACT

A nasal spray formulation and a method of using a locally acting sodium channel blocker to treat pain is disclosed, wherein the nasal spray formulation comprises from about 5% to about 30% w/v of a locally active sodium channel blocker, from about 0.25% to about 5% w/v of a buffering agent, and from about 5 to about 99% w/v of a pharmaceutically acceptable carrier for nasal administration. The nasal spray formulation is preferably contained in a mechanical multi-dose pump which sprays a unit dose of the nasal spray formulation with a wide plume and small droplet size, such that the unit dose is administered by actuating the mechanical multi-dose spray pump device and spraying a volume of the nasal spray formulation into each nostril of a human subject. Preferably, the nasal spray formulation does not include a preservative.

19 Claims, 2 Drawing Sheets

THERAPEUTIC COMPOSITION OF INTRANASAL LIDOCAINE

FIELD OF THE INVENTION

The present invention discloses a (preferably) preservative free intranasal composition in multi-dose or bi-dose or unit-dose spray container to treat the pain associated to tri-geminal neuralgia, facial neuropathic pain, facial cancer induced neuropathic pain, migraine pain, and cluster headache pain.

Preservative free nasal formulations unveil a few interesting aspects. Nasal formulations intended for use over a long period of time are generally preserved. However, it has now been recognized that preservatives have a negative effect on the ciliated tissue in the nasal cavity. The ciliary epithelium plays a decisive role in the function of the nose. The movement of the cilia is responsible for transporting inhaled particles that are trapped on the nasal mucosa; the debris is guided towards the throat and subsequently removed by swallowing. This clearing function prevents foreign particles from reaching the lungs. The effect of preservatives on the ciliary beat frequency can be described as cilio inhibiting. In the case of a nasal infection such as perennial rhinitis the mucus in the nasal cavity is highly contaminated and it is important to remove the infected mucus as quickly as possible. To treat the infection, the patient applies a preserved nasal spray up to three times a day over a period of up to three months in cases of a severe allergy. However, the preservatives do exactly the opposite and slow down the clearing of the mucus. The German health authority (BfArM) recently published a risk statement concerning the widely used preservative Benzalkonium chloride. The patient information leaflet must mention that frequent administration of Benzalkonium chloride irritates the nasal mucosa and therefore alternative unpreserved products should be used. The same holds true for benzyl alcohol, which is commonly used as a preservative (see, e.g., U.S. Pat. No. 8,580,282). In the National Library of Medicine HSDB database, benzyl alcohol is noted as being irritating to the skin at levels of 3% or greater, and at a concentration of 0.225 mg/ml in triamcinolone acetonide (TA) following intravitreal injection benzyl alcohol caused ultrastructural damage and impaired human retinal pigment epithelial cell function at 2 hours.

Unpreserved nasal products are common in unit- and bi-dose delivery systems, which deliver one or two doses into the nostril(s). These devices are disposable, thus, there is no risk of contamination during the period of use. Multi-dose systems are different in functional design and are to be used daily by the patient for a period of up to six months. In the case of unpreserved content, the drug-delivery product will certainly become contaminated during the period of use.

Trigeminal neuralgia (TN) is defined by The International Association for The Study of Pain (IASP), as "sudden usually unilateral severe, brief, stabbing, recurrent episodes of pain in the distribution of one or more branches of the trigeminal nerve". The International Headache Society (IHS) divides Trigeminal Neuralgia into two distinct categories: "classical" and "symptomatic" (secondary) TN. Classical TN includes those patients in which no identifiable cause can be found for their TN other than a vascular compression of the trigeminal nerve. Symptomatic TN describes those patients in which an identifiable cause can be found, other than a vascular compression, such as a tumour, arteriovenous malformation or multiple sclerosis (MS). Studies in Europe have shown that trigeminal neuralgia results in considerable interference with activities of daily living that is comparable to other neuropathic pain conditions and could lead to suicide.

There is no specific treatment for Trigeminal neuralgia. Treatments are strictly palliative, targeted to the provision of symptomatic pain relief with the treatment goal to reduce pain to tolerable levels. The current available pharmacological treatments for the treatment of symptomatic relief of TN include antidepressants, serotonin noradrenaline reuptake inhibitors (SNRIs), selective serotonin reuptake inhibitors (SSRIs), anti-epileptics, and opioids. For this particular indication, drugs should act fast and just locally while systemic absorption should be as low as possible to avoid systemic side effects which are linked with typical oral formulations of comparable drug substances. The present invention of intra nasal delivery of sodium channel local analgesic will provide fast onset of pain relief and less associated side effects.

OBJECTS AND SUMMARY OF THE INVENTION

It is an object of the present invention to provide formulations and methods for providing pain relief in humans and animals by administering a preservative-free intranasal dose of a local anesthetic formulation for the treatment of tri-geminal neuralgia, facial neuropathic pain, facial cancer induced neuropathic pain, migraine pain, and cluster headache pain.

In accordance with the above object and others, the present invention is directed in part to a nasal spray formulation of a locally acting sodium channel blocker to treat pain, comprising from about 5% to about 30% w/v of a locally active sodium channel blocker, from about 0.25% to about 5% w/v of a buffering agent, and from about 5 to about 99% w/v of a pharmaceutically acceptable carrier for nasal administration, the nasal spray formulation having a viscosity from about 0.8 to about 1.1 cps and contained in a mechanical multi-dose pump which sprays a unit dose of the nasal spray formulation with a wide plume and small droplet size, such that the unit dose is administered by actuating the mechanical multi-dose pump and spraying a volume of the nasal spray formulation into each nostril of a human subject. The present invention is further directed in part to a unit dose of a nasal spray formulation of a locally acting sodium channel blocker to treat pain, comprising from about 5% to about 30% w/v of a locally active sodium channel blocker, from about 0.25% to about 5% w/v of a buffering agent to provide a pH from about pH 4.5 to about pH 7, and from about 5 to about 99% w/v of a pharmaceutically acceptable carrier for nasal administration, the nasal spray formulation having a viscosity from about 0.8 to about 1.1 cps and contained in a mechanical multi-dose spray pump device, the unit dose being delivered in volume of about 0.04 ml to about 0.2 ml as a wide plume defined by a mean spray angle from about 50 to about 95 degrees and a small droplet size defined by a mean Dv10 from about 10 to about 30 μm, a mean Dv50 is from about 20 to about 60 μm, and a mean Dv90 is from about 80 to about 120 μm, the unit dose when sprayed into each nasal cavity of a human patient being therapeutically effective to treat a condition selected from the group consisting of tri-geminal neuralgia, facial neuropathic pain, facial cancer induced neuropathic pain, migraine pain, and cluster headache pain.

Preferably, each spray administered by actuating the mechanical multi-dose spray pump device provides a volume from about 40 μl to about 120 μl. In certain preferred embodiments, the mechanical multi-dose pump provides a volume of about 100 µl (0.100 ml). When administered in a unit dose intranasally, the nasal spray formulation is therapeutically effective to treat pain associated with a condition selected from the group consisting of tri-geminal neuralgia, facial neuropathic pain, facial cancer induced neuropathic pain, migraine pain, and cluster headache pain. In certain preferred embodiments, the locally active sodium channel blocker is a local anesthetic selected from the group consisting of lidocaine, bupivacaine, ropivacaine, mepivacaine, tetracaine, and mixtures of any of the foregoing. In certain preferred embodiments, the nasal spray formulation further comprises a second active agent such as epinephrine, a vasodilator, an anticonvulsant drug, a muscle relaxant, an analgesic, and combinations thereof. In certain preferred embodiments, the pharmaceutically acceptable carrier for nasal administration comprises water. In certain preferred embodiments, the nasal spray formulation when sprayed provides a droplet size from about 5 to about 500 microns.

In preferred embodiments, the mechanical multi-dose spray pump device includes a spring-loaded valve located directly below the opening of the tip orifice such that the mechanical multi-dose pump does not allow any microbes to migrate from any surfaces or contacted liquids into the system and/or the mechanical multi-dose pump includes a sterile filtration system which includes hydrophobic filter membranes with pore sizes less than 0.2 µm, and the nasal spray formulation does not include a preservative.

In certain preferred embodiments, the locally active sodium channel blocker is lidocaine and a unit dose provides from about 5 mg to about 20 mg lidocaine sprayed into the nasal cavity of the human subject.

The nasal spray formulation is preferably administered intranasally by spraying about 1-2 sprays in each nostril, for a total of about 4 sprays in every application to provide an effective dose of the locally active sodium channel blocker. When the locally active sodium channel blocker is lidocaine and the intranasal formulation is administered at about 4-hour intervals.

In certain preferred embodiments, the mechanical multi-dose spray pump device when actuated provides a small droplet size (µm) wherein the mean Dv10 is from about 10 to about 30 µm, the mean Dv50 is from about 20 to about 60 µm, and the mean Dv90 is from about 80 to about 120 µm. The mechanical multi-dose pump preferably provides a mean spray angle from about 50 to about 95 degrees. Preferably, the spray pattern of the multi-dose pump spray preferably provides a mean $D_{min}$ from about 10 to about 45 mm, a $D_{max}$ from about 40 to about 70 mm, an ovality ratio from about 0.5 to about 2 mm. Ovality ratio is calculated as $D_{max}$ divided by $D_{min}$. In certain embodiments, the spray pattern of the multi-dose pump spray has a % area from about 12 to about 22 mm.

The present invention is further directed to a method of treating pain associated with a condition selected from the group consisting of tri-geminal neuralgia, facial neuropathic pain, facial cancer induced neuropathic pain, migraine pain and cluster headache pain, comprising incorporating a nasal spray formulation containing a locally acting sodium channel blocker to treat pain, comprising from about 5% to about 30% w/v of a locally active sodium channel blocker, from about 0.25% to about 5% w/v of a buffering agent, and from about 5 to about 99% w/v of a pharmaceutically acceptable carrier for nasal administration, the nasal spray formulation having a viscosity from about 0.8 to about 1.1 cps and contained in a mechanical multi-dose spray pump device which sprays a unit dose of the nasal spray formulation with a wide plume and small droplet size when actuated, the unit dose being therapeutically effective to treat a condition selected from the group consisting of tri-geminal neuralgia, facial neuropathic pain, facial cancer induced neuropathic pain, migraine pain, and cluster headache pain. In certain preferred embodiments, the mechanical multi-dose pump (i) includes a spring-loaded valve located directly below the opening of the tip orifice such that the mechanical multi-dose pump does not allow any microbes to migrate from any surfaces or contacted liquids into the system; or (ii) includes hydrophobic filter membranes with pore sizes less than 0.2 µm; or (iii) both (i) and (ii) above, and the nasal spray formulation does not include a preservative. In certain preferred embodiments, the locally active sodium channel blocker is a local anesthetic selected from the group consisting of lidocaine, bupivacaine, ropivacaine, mepivacaine, tetracaine, and mixtures of any of the foregoing. In certain especially preferred embodiments, the locally active sodium channel blocker is lidocaine and a unit dose provides from about 5 mg to about 20 mg lidocaine sprayed into the nasal cavity of the human subject.

In certain preferred embodiments of the method, the mechanical multi-dose pump provides a volume of about 0.04 ml (40 µl) to about 0.2 ml (200 µl), and in certain embodiments preferably from about 0.08 ml to about 0.12, and in certain embodiments about 0.10 ml. The nasal spray formulation is preferably administered by actuating the mechanical multi-dose pump and spraying about 1-2 sprays in each nostril of a human subject, for a total of about 4 sprays in every application to provide an effective dose of the locally active sodium channel blocker. When the locally active sodium channel blocker is lidocaine, the intranasal formulation may be administered at about 4-hour intervals.

The method in certain embodiments further comprises incorporating a second active agent into the nasal spray formulation, the second active agent selected from the group consisting of epinephrine, a vasodilator, an anticonvulsant drug, a muscle relaxant, an analgesic drug which is not a locally active sodium channel blocker, and combinations of any of the foregoing.

In the method, in certain preferred embodiments, the mechanical multi-dose pump is provided such that when actuated, the mechanical multi-dose pump provides a small droplet size (µm) wherein the mean Dv10 is from about 10 to about 30 µm, the mean Dv50 is from about 20 to about 60 µm, and the mean Dv90 is from about 80 to about 120 µm. Preferably, the mechanical multi-dose pump provides a mean spray angle from about 50 to about 95 degrees. Preferably, the spray pattern of the mechanical multi-dose pump spray preferably provides a mean $D_{min}$ from about 15 to about 45 mm, a $D_{max}$ from about 40 to about 70 mm, an ovality ratio from about 0.5 to about 2 mm, and a percentage (%) area from about 12 to about 22 mm.

In certain embodiments, the pharmaceutically acceptable carrier for nasal administration comprises or consists of water.

In certain preferred embodiments, the method further comprises comprising arranging the mechanical multi-dose pump such that when actuated, it provides a spray droplet size from about 5 to about 500 microns.

In certain preferred embodiments, the drug (e.g., local anesthetic) comprises from about 5 to about 20% w/v of the composition. In certain preferred embodiments, the composition includes a buffering agent from about 0% to about 5% w/v, and in certain preferred embodiments from about 0.25% to about 5% w/v of the composition. In certain preferred embodiments, the solvent carrier comprises purified water in an amount from about 5% to about 99% w/v. In certain preferred embodiments, the composition comprises a (optional) preservative in an amount from about 0.25% to about 5% w/v. In certain embodiments, the viscosity of the composition is from about 0.8 to about 1.1 cps.

For purposes of the present invention, the terms "active agent", "drug" and medicament are used interchangeably, and are meant to encompass a single drug or multiple drugs (two or more) contained in the nasal spray formulations of the invention.

All numbers expressing quantities of ingredients, reaction conditions, and so forth used in the specification and claims are to be understood as being modified in all instances by theterm "about." Accordingly, unless indicated to the contrary, the numerical parameters set forth in the specification and attached claims are approximations that may vary depending upon the desired properties sought to be obtained by the present invention. At the very least, and not asan attempt to limit the application of the doctrine of equivalents to the scope of the claims, each numerical parameter should be construed in light of the number of significant digits and ordinary rounding approaches.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein, the singular form "a", "an" and "the" include plural references unless the context clearly dictates otherwise. For example, the term "a compound" or "at least one compound" may include a plurality of compounds, including mixtures thereof.

The term "local anesthetic" means any drug or mixture of drugs that provides local numbness and/or analgesia.

As used herein, the term "unit dose" refers to physically discrete units suitable as unitary dosages for mammalian subjects, each unit containing as the active ingredient a predetermined quantity of the active agent (e.g., local anesthetic).

As used herein, the term "comprising" is an inclusive term interpreted to mean containing, embracing, covering or including the elements listed following the term, but not excluding other unrecited elements.

A "therapeutically effective amount" means the amount that, when administered to an animal for treating a disease, is sufficient to effect treatment for that disease.

As used herein, the term "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

For purposes of the present invention, the term "active agent" is meant to encompass, but not be limited to, a drug. The term active agent is further meant to encompass a single active agent, or multiple (two or more) active agents present in the formulation.

As used herein, droplet size distribution may be characterized by the following metrics: volume distribution (Dv10, Dv50, Dv90) and Span and percentage (%) less than 9 μm per the FDA CMC guidance on Nasal spray and Inhalation Solution, Suspension and Spray Drug Products-Chemistry, Manufacturing and Controls Documentation, July 2002. Dv10 means, for example, the diameter for which 10% of the total spray volume is made up of droplets of equal or lesser diameter. Dv50 means, for example, the diameter for which 50% of the total spray volume is made up of droplets of equal or lesser diameter. Dv90 means, for example, the diameter for which 90% of the total spray volume is made up of droplets of equal or lesser diameter.

As used herein, $D_{max}$ is defined as the longest diameter measured on the resulting spray pattern image.

As used herein, $D_{min}$ is defined as the shortest diameter measured on the resulting spray pattern image.

For purposes of the present invention, spray pattern may be characterized by one or more of the following metrics: $D_{max}$, $D_{min}$, ovality ratio, and % area per the FDA guidance for the Industry: Bioavailability and Bioequivalence Studies for Nasal Aerosols and Nasal Sprays for Local Action.

As used herein, the ovality ratio is the ratio of $D_{max}$ to $D_{min}$. This ratio provides a quantitative value for the overall shape of the spray.

As used herein, spray angle means the angle of the emitted plume measured from the vertex of the spray cone and spray nozzle, as per FDA Guidance for the Industry.

As used herein, plume width means the width of the plume at a given distance from the spray nozzle, as per FDA Guidance for the Industry.

For purposes of the present invention, all percentages described herein are "w/w" unless otherwise specified.

The present invention in certain embodiments is directed to a method of treating pain comprising the administration of a preservative free intranasal composition in multi-dose or bi-dose or unit-dose spray via the utilization of a (mechanical pump) metered dose spray device.

The present invention is a preservative-free multi dose and or unit dose and or bi-dose of an aqueous local anesthetic (e.g., a sodium channel blocker such as lidocaine) nasal spray formulation, this formulation comprising liquid droplets of lidocaine, a pharmaceutically acceptable salt thereof, or derivative thereof; and a pharmaceutically acceptable solvent carrier; said droplets having a size distribution of from about 5 microns to about 500 microns. The present invention is directed to a method of treating pain comprising the utilization of a spray device.

The present invention discloses a (preferably) preservative free intranasal composition in multi-dose or bi-dose or unit-dose spray container to treat the pain associated to tri-geminal neuralgia, facial neuropathic pain, facial cancer induced neuropathic pain, migraine pain, and cluster headache pain. In certain embodiments, the intranasal spray formulation of the invention may be used for treating general pain, neuropathic pain (e.g., erythromelalgia, post-herpetic neuralgia (PHN), fibromyalgia and/or complex regional pain syndrome (CRPS), among others).

The liquid pharmaceutical composition of this invention contains a pharmaceutically effective amount of sodium channel blocker (e.g., lidocaine) in a pharmaceutically acceptable liquid carrier e.g. purified water, and an optional buffer, e.g. citrate, to maintain the pH at about pH 3 to about 8 and preferably about pH 3 to about pH 6 and an optional complexing agent, e.g. citrate or EDTA, to inhibit the precipitation of drug substance from the aqueous medium.

Lidocaine (xylocaine) was introduced as a local anesthetic in 1948. Local anesthetics act by preventing the generation and conduction of nerve impulse. Their primary site of action is the cell membrane. They block conduction by decreasing or preventing the large transient increase in the permeability of excitable membranes to Na+ that normally is produced by a slight depolarization of the membrane. This action of local anesthetics is due to their direct interaction with voltage gated Na+ channels. As the anesthetic action progressively develops in a nerve, the threshold for electrical excitability gradually increases, the rate of rise of the action potential declines, impulse conduction slows, and the safety factor for conduction decreases; these factors decrease the probability of propagation of the action potential, and nerve conduction fails. Bupivacaine, a longer acting variant of lidocaine is a preferred local analgesic.

The degree of block produced by a given concentration of local anesthetic depends on how the nerve has been stimulated and on its resting membrane potential. Thus, a resting nerve is much less sensitive to a local anesthetic than is one that is repetitively stimulated; higher frequency of stimulation and more positive membrane potential cause a greater degree of anesthetic block. These frequency and voltage dependent effects of local anesthetics occur because the local anesthetic molecule in its charged form gains access to its binding site within the pore only when the Na+ channel is in an open state and because the local anesthetic molecule binds more tightly to and stabilizes the inactivated state of the Na+ channel. Local anesthetics exhibit these properties to different extents depending on their pKa, lipid solubility and molecular size.

Lidoderm patch is cumbersome to use. It is supplied as a 10 cm×14 cm patch. The patient is instructed to apply three patches to the most painful area once for up to 12 hours. Per the package insert, the site of patch application may develop erythema, edema, bruising, papules, vesicles, discoloration, depigmentation, burning sensation, pruritus and abnormal sensation which is reversed upon patch removal. The patch is not patient friendly more so when the pain presents itself outside the upper body and trunk area specifically in the facial area (myofascial pain). It is anticipated that the present invention, which is an easy to use proprietary dermal spray formulation to overcome many of the disadvantages of patch application while still providing pain relief in patients with PHN. An intranasal formulation would provide application convenience.

In certain preferred embodiments of the invention, therapeutically effective amounts of one or more pharmaceutically acceptable local anesthetics are incorporated into the formulations of the invention. Examples of local anesthetic agents useful in the formulations of the invention include amide type local anesthetics, such as mepivacaine, lidocaine, mepivacaine, etidocaine and prilocaine; ester type local anesthetics, such as procaine, chloroprocaine, and tetracaine; and antihistamine-like anesthetics, such as benadryl. These anesthetics can be present in the anesthetic pharmaceutical combination alone or as a mixture of two or more thereof. Thus, examples of useful local anesthetics are lidocaine, bupivacaine, dibucaine, tetracaine, etidocaine, mepivacaine, ropivacaine, benzocaine, ambucaine, amylocaine, butamben, 2-chloroprocaine, cyclomethycaine, ethyl aminobenzoate, euprocin, levoxadrol, orthocaine, piperocaine and parethoxycaine. In certain preferred embodiments, the local anesthetic is bupivacaine, ropivacaine, dibucaine, procaine, chloroprocaine, prilocaine, mepivacaine, etidocaine, tetracaine, lidocaine, and xylocaine, or mixtures thereof. The phrase "local anesthetic" also can include drugs of a different class than those traditionally associated with local anesthetic properties, such as morphine, fentanyl, and agents which, for example, can provide regional blockade ofnociceptive pathways (afferent and/or efferent). In other embodiments, the active agent is an anesthetic such as a barbiturate (e.g., amobarbital, methohexital, thiamylal, thiopental), a benzodiazepine (e.g., diazepam, lorazepam, midazolam), or etomidate, ketamine, or propofol. Other compounds which may be used as a local anesthetic in the gel formulations of the invention include antihistamine-like anesthetics, such as benadryl. Phenol may also be used as the local anesthetic. Those skilled in the art will recognize other agents which have been recognized to possess local anesthetic properties, such as the substituted piperidines and pyrollidines described in U.S. Pat. No. 4,302,465 (Aberg, et al.) and the aminoindane piperidine compounds described in U.S. Pat. No. 6,413,987 (Aberg, et al.), both of which patents are hereby incorporated by reference. The term local anesthetic is also deemed for purposes of the present invention to encompass the local anesthetic base or a pharmaceutically acceptable salt, polymorph, complex or pro-drug thereof. Many other examples of both drugs and local anesthetics will be readily apparent to those skilled in the art, and are considered to be encompassed by this disclosure and appended claims.

The local anesthetic can be in the form of a salt, for example, the hydrochloride, bromide, acetate, citrate, carbonate, sulfate or phosphate. In certain embodiments, the local anesthetic agent is in the form of a free base. Local anesthetics can be in the form of a salt, for example, the hydrochloride, bromide, acetate, citrate, carbonate or sulfate, or in the form of a free base. Many of the local anesthetics are conventionally used in the form of their acid addition salts, as this provides solubility in aqueous injection media. In certain embodiments of the invention, it is desirable to use the local anesthetics in free base form, or with only a small proportion of the acid addition salt of the local anesthetic present (addition of small quantities of the acid addition salt may provide enhanced release if desired). The free base generally provides a slower initial release and avoids an early "dumping" of the local anesthetic at the injection site. Preferred local anesthetic agents include, e.g., lidocaine, bupivacaine, orropivacaine.

In certain preferred embodiments, the dose of local anesthetic contained in a unit dose is from about from about 1 mg to about 30 mg, based on a unit dose of lidocaine. In other preferred embodiments, the dose is from about 5 mg to about 20 mg, and preferably from about 5 mg to about 15 mg. In certain preferred embodiments, the unit dose of local anesthetic is 10 mg lidocaine, or a therapeutically equivalent amount of another local anesthetic. One skilled in the art understands how to determine equipotent doses of local anesthetics. Maximum doses and duration of action of the following local anesthetics is generally recognized: lidocaine-4.5 mg/kg, duration 0.75-1.5 hours; mepivacaine—4.5 mg/kg, duration 1-2 hours; prilocaine—8 mg/kg, duration 0.5-1 hour; bupivacaine 3 mg/kg, duration 1.5-8 hours; ropivacaine 3 mg/kg, duration 1.5-8 hours; chloroprocaine—12 mg/kg, duration 0.5-1 hour; procaine 12 mg/kg, 0.5-1 hour; cocaine—3 mg/kg, duration 0.5-1 hour; tetracaine—3 mg/kg, duration 1.5-6 hours.

In the present invention, a nasal spray was prepared by adding the drug, optional buffering agent, to the solvent while stirring the solution to ensure complete dissolution of the drug and excipients. The formulations were stored in glass vials sealed tightly with metered dose spray pump.

In certain preferred embodiments, the active agent(s) (drug(s)) is a combination of therapeutically effective amounts of two different local anesthetics (e.g., bupivacaine and lidocaine combination) for use in treating pain.

The composition contains preferably from about 1% to about 30% w/v of the at least one medicament (drug), more preferably from about 5% to about 20% w/v of the at least one drug and most preferably about 10% w/v of the at least one drug.

In certain preferred embodiments, the drug is supersaturated in the formulation. It is believed that the closer to supersaturation the drug is in the formulation, the more permeation is obtained when the drug is administered, e.g., by spraying into nasal cavities.

In certain preferred embodiments, the active agent(s) (drug(s)) is a combination of therapeutically effective amounts of a local anesthetic (e.g., lidocaine) and ketamine and or amitriptyline for use in treating pain. In certain embodiments, the active agent comprises a combination of lidocaine hydrochloride and a second active agent selected from the group consisting of ketamine, amitriptyline, and combinations thereof. In certain preferred embodiments, the active agent(s) (drug(s)) is a combination of therapeutically effective amounts of a local anesthetic (e.g., lidocaine) and meloxicam and or other muscle relaxant for use in treating pain. In certain embodiments, the active agent comprises a combination of lidocaine hydrochloride and a second active agent selected from the group consisting of meloxicam, tizanidine, and combinations thereof.

In certain preferred embodiments, the active agent(s) (drug(s)) is a combination of therapeutically effective amounts of a local anesthetic (e.g., lidocaine) and epinephrine and or vasodilators for use in treating pain. In certain embodiments, the active agent comprises a combination of lidocaine hydrochloride and a second active agent selected from the group consisting of epinephrine, vasodilators, and combinations thereof. Suitable vasodilators include but are not limited to diltiazem, clonidine, nifedipine, verapamil, isosorbide-5-mononitrate, organic nitrates, agents used in treatment of heart disorders, and analogues thereof.

In certain preferred embodiments, the active agent(s) (drug(s)) is a combination of therapeutically effective amounts of a local anesthetic (e.g., lidocaine) and carbamazepine and/or anticonvulsant drug for use in treating pain. In certain embodiments, the active agent comprises a combination of a local anesthetic (e.g., lidocaine hydrochloride) and a second active agent selected from the group consisting of carbamazepine, anticonvulsant drug, and combinations thereof.

The formulations of the invention can include two or more of the above-mentioned ingredients (drugs) or pharmaceutically acceptable salts, complexes or derivatives thereof, as well.

Optional Excipients

In addition to the active agent(s) (e.g., local anesthetic), the nasal spray formulation may additionally include physiologically acceptable components such as sodium chloride and like materials conventionally used to achieve isotonicity with typical body fluids, pH buffers to establish a physiologically compatible pH range and to enhance the solubility of the anesthetic present, vasodilators such as epinephrine, preservatives, stabilizers and antioxidants and thelike.

In certain other embodiments, an additional surfactant (co-surfactant) and/or buffering agent can preferably be combined with one or more of the pharmaceutically acceptable vehicle previously described herein so that the surfactant and/or buffering agent maintains the product at an optimal pH for stability. The surfactant and/or buffering agent may also prevent the initial stinging or burning discomfort associated with administration of the active agent on the skin (e.g, local anesthetic).

In certain other embodiments, an additional anti-oxidant and/or stabilizing agent can preferably be combined with one or more of the pharmaceutically acceptable vehicles previously described herein so that the anti-oxidant and/or stabilizing agent maintains the drug product at an optimal impurity level for stability. The anti-oxidant and/or stabilizing agent also prevents the initial degradation of active agent during the manufacturing process. The anti-oxidant may be selected, e.g., from ascorbic acid, EDTA, trolamine, tocopherol, propyl galate, sodium sulfite, sodium bisulfate, and mixtures of any of the foregoing. The optional stabilizing agent may be, e.g., an anti-oxidant and/or pH modifier. In other embodiments, the optional stabilizing agent may be a cyclodextrin used as an inclusion complex. Pharmaceutically acceptable pH adjusting agents include, by way of example and without limitation, hydrochloric acid, citric acid, sodium acetate, sodium hydroxide, sodium phosphate or lactic acid. In certain embodiments a buffer selected from, e.g., citric acid monohydrate, an acetate buffer (e.g., sodium acetate, ammonium acetate) and succinate buffers is included, preferably to maintain the formulation at a pH from about 3 to about 9, and in certain preferred embodiments from about pH 4.5 to about pH 7, or about pH 5.5. In certain preferred embodiments, the injectable formulations after dilution with, e.g., water and/or other commonly available and suitable solutions for intranasal application, the pH will preferably be a physiologically compatible pH range.

Optional antimicrobial agents in bacteriostatic or fungistatic concentrations may be added to the formulations which are packaged in multiple dose containers, which include phenols or cresols, mercurials, benzyl alcohol, chlorobutanol, methyl and propyl p-hydroxybenzoic acid esters, thimerosal, benzalkonium chloride, benzethonium chloride, boric acid, p-hydroxybenzoates, phenols, chlorinated phenolic compounds, alcohols, quarternary compounds, mercurials, mixtures of the foregoing and the like. Optional isotonic agents include, by way of example and without limitation, sodium chloride and dextrose. Optional suspending and dispersing agents include sodium carboxymethylcelluose, hydroxypropyl methylcellulose and polyvinylpyrrolidone. Optional emulsifying agents include Polysorbate 80 (TWEEN® 80). Pharmaceutically acceptable pH adjusting agents include, by way of example and without limitation, sodium hydroxide, hydrochloric acid, citric acid or lactic acid. In some embodiments of the present invention, the pH is adjusted using a pharmaceutically acceptable buffer or acidifying agent, particularly if the active agent is in its base form (e.g., lidocaine base).

In certain other embodiments, the formulation may be made isotonic via the addition of a tonicity agent conventionally used to achieve isotonicity with typical body fluids, pH buffers to establish a physiologically compatible pH range, such as but not limited to any pharmaceutically acceptable sugar, salt or any combinations or mixtures thereof, such as, but not limited to dextrose and sodium chloride. The tonicity agents may be present in an amount from about 100 mOsm/kg to about 500 mOsm/kg, or from about 200 mOsm/kg to about 400 mOsm/kg, or from about 280 mOsm/kg to about 320 mOsm/kg.

In certain preferred embodiments, the formulations of the present invention will have the following composition (% w/w):

| | |
|---|---|
| Active | 5-20% w/v |
| Buffering agent | 0.25-5% w/v |
| Purified water | 5-99% w/v |
| Preservative (optional) | 0.25-5 w/v |
| Viscosity: | 0.8-1.1 cps |

The formulation of the invention may contain preservatives to prevent microbial growth. Suitable preservatives for use in the present invention include, but are not limited to benzoic acid, boric acid, p-hydroxybenzoates, phenols, chlorinated phenolic compounds, alcohols, quaternary compounds, mercurials, mixtures of the foregoing and the like.

Preservative-Free Formulations

When using a preservative free multi-dose product, there are two ways for microorganisms to enter the system: (1) via the pump orifice; and (2) via the venting air which is replacing the dispensed liquid. In preserved formulations (conventional system), the added preservative controls microbial growth and no additional measures need to be taken to prevent microbial occupation via the orifice or venting air. If the formulation does not contain preservatives, the device must be able to keep microorganisms out the system. The highest risk of contamination typically comes from the orifice, because it may come in contact with skin and mucosa as well as with infected body fluids.

To prevent microbial contamination in the present invention, in certain preferred embodiments with respect to the pump orifice there is included a mechanical approach to minimize interaction between parts of the device and the formulation. For example, in certain preferred embodiments, a spring-loaded valve is located directly below the opening of the tip orifice and does not allow any microbes to migrate from any surfaces or contacted liquids into the system. Thus, the orifice is "sealed" under resting conditions. The tip seal keeps the system closed until a defined pressure is reached by actuating the system. Then, the system will open and the formulation is forced through the orifice with a higher pressure than needed to open the valve. When the pressure drops at the end of the actuation the tip seal will immediately close the orifice with an outward movement. This prevents backflow of potentially contaminated medication or other liquid.

To prevent microbial contamination in additional or alternative embodiments, the microbial contamination of the formulation is avoided via venting air by using a sterilefiltration system. The venting air in pressure balanced systems are forced though sterile filters with pore sizes less than 0.2 μm. The filter membranes are normally hydrophobic which prevents leakage from liquids out of the container via the venting system.

During the manufacturing process, the drug product solution (formulation) will preferably be sterilized and filling and spray pump assembly will be performed under the aseptic condition to avoid any microbial contamination during the drug product manufacturing and packaging.

Mechanical Sprayer

In certain preferred embodiments, the compositions of the present invention are sprayed into the nostril(s) of the subject (e.g., human patient) via a mechanical multi-dose pump having a mean spray volume, e.g., from about 40 ul to about 120 ul. Preferably, the multi-dose pump sprays with a wide plume and small droplet size. A representative multi-dose pump which is useful is a Pfeiffer SAP-62602 multi-dose pump (130 ul/actuation) (Pfeiffer, Princeton, NJ). By "wide plume" for the purposes of the present invention it is meant that the spray pump pattern preferably has a mean spray angle from about 50 to about 95 degrees, more preferably from about 60 to about 90 degrees, and most preferably from about 70 to about 80 degrees; and a mean plume width (mm) from about 20 to about 70 mm, more preferably from about 30 to about 60 mm, and most preferably from about 42 to about 52 mm. The term "small droplet size" for purposes of the present invention means a droplet size (μm) wherein the mean Dv10 is from about 10 to about 30 μm, the mean Dv50 is from about 20 to about 60 μm, and the mean Dv90 is from about 80 to about 120 μm. The spray pattern of the multi-dose pump spray preferably provides a mean $D_{min}$ from about 15 to about 45 mm, a $D_{max}$ from about 40 to about 70 mm, an ovality ratio from about 0.5 to about 2 mm, and a % area from about 12 to about 22 mm.

In certain preferred embodiments of the invention, a multi-dose pump (metering device) is used which has features described in U.S. Patent Publication No. 2007/026090A1, the disclosure of which is hereby incorporated by reference in its entirety, e.g., a metering device for at least one medium, with a pump unit, which is operatively connected to a medium reservoir for the purpose of discharging a medium, and with a venting device, which is assigned to the medium reservoir and/or to the pump unit and which has a venting channel to which a filter membrane is assigned. Therein, a metering device is described in which the filter membrane has a reduced effective cross section compared to known filter membranes. The effective cross section is the product of the number of pores provided in the filter membrane and the mean free cross section of these pores. Filter membranes are designed in particular as stretched or perforated plastic films or as sinter materials, but also as metal foils, and, depending on the chosen production method, they can vary within a wide range in terms of the number of pores and the free cross sections of the pores. The pores or channels formed in the plastic film or in the sinter material in each case have a free cross section that can be determined on the basis of the maximum molecule size that is able to pass through the channel. The effective cross section is in direct relation to the diffusion rate of the filter membrane. A large number of channels or pores and a large free cross section of the individual channels or pores results in a large effective cross section and permits a high diffusion rate, i.e. a large number of molecules can pass through the filter membrane even at a low pressure difference. In certain preferred embodiments, the effective surface area of the filter membrane is smaller than 1.4 mm$^2$, preferably smaller than 0.6 mm$^2$, particularly preferably smaller than 0.2 mm$^2$. In another embodiment, in order to obtain the reduced effective cross section, a mean free cross section of pores in the filter membrane is designed smaller than in known filter membranes. This means that the size of the gas molecules that are able to pass through the filter membrane is reduced. In another embodiment, the filter membrane has a mean pore number of less than 1 million pores per mm$^2$, preferably of less than 600,000 pores per mm$^2$, particularly preferably of less than 300,000 pores per mm$^2$.

In certain preferred embodiments of the invention, a multi-dose pump (metering device) is used which has features described in U.S. Pat. No. 8,382,010, the disclosure of which is hereby incorporated by reference in its entirety, which describes a dosing device with a manually actuatable pumping means, a pumping chamber and an inlet valve constructed as a slide valve and which is movable by means of a dosing stroke in a sealing manner in a dosing channel in its closed position and which defines a dosing volume for the pumping chamber, the dosing channel opening on the inlet side into an inlet area. The device preferably further comprises at least one gas flow capillary tube is at one end open to the environment and at its other end into a medium reservoir, and on the end facing said medium reservoir is provided a filter unit. This makes it possible to ventilate the medium reservoir without bringing about a contamination of the medium by the ambient air. In certain preferred embodiments, the multi-dose pump comprises a manually actuatable pumping arrangement having a pumping chamber and an inlet valve constructed as a slide valve, the slide valve having a cylindrical dosing channel comprised of upper and lower parts that are coaxially aligned with a pumping axis, a wall surface of the lower part having circumferentially spaced flow profilings and a piston having a sealing lip configured to slide lengthwise of the dosing channel along the pumping axis while sequentially slidingly engaging a wall surface of the upper part and the wall surface of the lower part of the dosing channel, the dosing channel on an inlet side opening into an inlet area of the lower part remote from the upper part, the inlet area having the flow profilings configured to cause opening of the slide valve upon movement of the sealing lip to the inlet area, the sealing lip being in a closed position of the slide valve while sealingly slidingly engaging the wall surface of the upper part and becoming opened in response to the sealing lip engaging the inlet area of the lower part caused by the flow profilings allowing medium to flow past the sealing lip from a medium reservoir through the flow profilings into the dosing channel and to the pumping chamber, the sealing lip being sealingly movable along the pumping axis over a dosing stroke in the dosing channel so that the slide valve defines a dosing volume for the pumping chamber. Preferably, the flow profilings are oriented in a longitudinal direction of the dosing stroke and are formed by longitudinal grooves extending parallel to the pumping axis over an axial length of the inlet area, and the flow profilings are arranged in a mutually uniformly distributed manner in a circumferential direction of the inlet area. In certain preferred embodiments, the inlet area and the dosing channel are provided on separate components. The components are preferably joined together in a coaxially interengaging manner, and on facing circumferential surfaces the components are profiled in such a way that between the circumferential surfaces at least one gas flow capillary tube is formed between axially facing front edges of the circumferential surfaces. Preferably, the gas flow capillary tube is open at a first end to an environment outside the device and is open at a second end to a medium reservoir, and the second end faces the medium reservoir and is provided with a filter unit.

Treatment

The intranasal formulation of the invention may be packaged in a multi-dose orbi-dose or unit-dose spray container to treat the pain associated to tri-geminal neuralgia, facial neuropathic pain, facial cancer induced neuropathic pain, migraine pain, and cluster headache pain.

When the intranasal formulation includes a local anesthetic (e.g., lidocaine, bupivacaine, ropivacaine, mepivacaine, tetracaine alone and or in combination), the mechanical sprayer device preferably delivers a volume of e.g., from about 0.04 ml to about 0.12 ml, or about 0.10 ml. In such instances, the formulation may be administered intranasally by spraying 1-2 sprays in each nostril, for a total of about 4 sprays in every application (to provide an effective dose). When the drug is lidocaine, the intranasal formulation is administered, e.g., at about 4-hour intervals.

In certain preferred embodiments, the treatment further comprises administering a second active agent selected from the group consisting of epinephrine, a vasodilator, an anticonvulsant drug, a muscle relaxant, an analgesic drug which is not a locally active sodium channel blocker, and combinations of any of the foregoing. Preferably, the second active agent is incorporated into the nasal spray formulation. However, the second active agent may be administered separately and concurrently or sequentially with the, e.g., local anesthetic.

DETAILED DESCRIPTION OF PREFERRED EMBODIMENTS

The following examples in accordance with the present invention are not to be construed as limiting the present invention in any manner and are only samples of the various formulations described herein.

Examples 1-3

A lidocaine preservative free intranasal formulation is prepared using the ingredients set forth in Table 1.

TABLE 1

| Composition | Example 1 mg/spray | Example 2 mg/spray | Example 3 mg/spray |
| --- | --- | --- | --- |
| Lidocaine | 10 | 10 | — |
| Lidocaine hydrochloride | — | — | 10 |
| Citric acid monohydrate | 3.50 | 3.25 | 3.0 |
| Purified Water | Qs | Qs | Qs |

The formulation is prepared as follows: Add citric acid monohydrate to purified water while stirring and mix till a clear solution is observed. Add lidocaine base or saltand other optional excipients while stirring and mix for 30 minutes till a clear solution is formed. Filter the clear solution using sterile 0.2 micron pore size filter and fill the solution in a glass bottle aseptically and tightly crimp metered dose mechanical pump.

Examples 4-5

A lidocaine preservative free intranasal formulation is prepared using the ingredients set forth in Table 2.

TABLE 2

| Composition | Example 4 mg/spray | Example 5 mg/spray |
| --- | --- | --- |
| Lidocaine hydrochloride | — | 10 |
| Lidocaine | 12.3 | — |
| Citric acid monohydrate | — | 3.50 |
| Purified Water | Qs | Qs |

The formulation is prepared as follows: Add citric acid monohydrate to purified water while stirring and mix till a clear solution is observed. Add lidocaine base or salt and other optional excipients while stirring and mix for 30 minutes till a clear solution is formed. Filter the clear solution using sterile 0.2 micron pore size filter and fill the solution in a glass bottle aseptically and tightly crimp metered dose mechanical pump.

The intranasal spray droplet size distribution of Example 5 is set forth in Table 3.

TABLE 3

Droplet Size Distribution Data for Metered Nasal Spray Lidocaine Solution

| Sample | Spray # | Dv10 (μm) | Dv50 (μm) | Dv90 (μm) | Span | % Droplets <10 μm | Pump Delivery (mg) |
|---|---|---|---|---|---|---|---|
| Example 5 | 1 | 17.87 | 45.15 | 102.10 | 1.866 | 1.747 | 92.4 |
|  | 2 | 16.77 | 42.29 | 98.05 | 1.922 | 2.252 | 94.9 |
|  | 3 | 15.92 | 40.69 | 96.56 | 1.982 | 2.696 | 92.9 |
| — | Mean | 16.85 | 42.71 | 98.90 | 1.923 | 2.232 | 93.4 |
|  | Stdev | 0.98 | 2.26 | 2.87 | 0.058 | 0.475 | 1.3 |
|  | % CV | 5.8 | 5.3 | 2.9 | 3.0 | 21.3 | 1.4 |
|  | Min | 15.9 | 40.7 | 96.6 | 1.866 | 1.747 | 92.4 |
|  | Max | 17.9 | 45.2 | 102.1 | 1.982 | 2.696 | 94.9 |

Example 6-8

A lidocaine preservative free intranasal formulation with combination of other drugs is prepared using the ingredients set forth in Table 4 for Examples 6-8.

TABLE 4

| Composition | Example 6 mg/spray | Example 7 mg/spray | Example 8 mg/spray |
|---|---|---|---|
| Lidocaine | 10 | 10 | 10 |
| Epinephrine | — | — | 0.01 |
| Meloxicam | 15 | — | — |
| Ketamine | — | 15 | — |
| Citric acid monohydrate | 3.50 | 3.25 | 3.0 |
| Purified Water | Qs | Qs | Qs |

The formulation is prepared as follows: Add citric acid monohydrate to purified water while stirring and mix till a clear solution is observed. Add lidocaine base or salt, combination drug and other optional excipients while stirring and mix for 30 minutes till a clear solution is formed. Filter the clear solution using sterile 0.2 micron pore size filter and fill the solution in a glass bottle aseptically and tightly crimp metered dose mechanical pump.

Example 9 (In-Vivo Study

An in-vivo study was performed in healthy rabbits to evaluate drug release from a lidocaine intranasal spray made in accordance with Example 4 and 5. A single dose study to evaluate the pharmacokinetics of two different formulations (Example 4 and 5) and access the local anesthetic activity of 10 mg lidocaine per spray (intranasal spray formulation), 0.10 ml per spray. A total of eighteen New Zealand white rabbits (both male and female) were used. These rabbits were randomized and divided into three groups (group 1 represent Example 5 formulation, group 2 represent Example 4 formulation and group 3 represents a placebo formulation); six rabbits in each group (3 males and 3 females).

The test formulations were administered as single spray in each nostril (total of two spray equivalent to 20 mg of lidocaine) using the metered spray pump. At 15 min post dose of test formulations, 100 μl of 5% formalin solution was administered subcutaneously on rabbit's right cheek near to middle of the nose and housed individually in test box. These rabbits were observed for 45 min (after formalin administration). Pain score was determined by measuring the number of seconds (amplitude) that the animal spent rubbing the injected area i.e., at right cheek. To determine the pharmacokinetics of test formulations, blood samples were collected at 0, 0.08, 0.25, 0.5, 0.75, 1, 2, 4, 8 and 24 hours post dose of test formulation from each rabbit.

The composition was sprayed using a Pfeiffer SAP-62602 multi-dose pump (130 μL/actuation) (Pfeiffer, Princeton, NJ).

Figure 1:
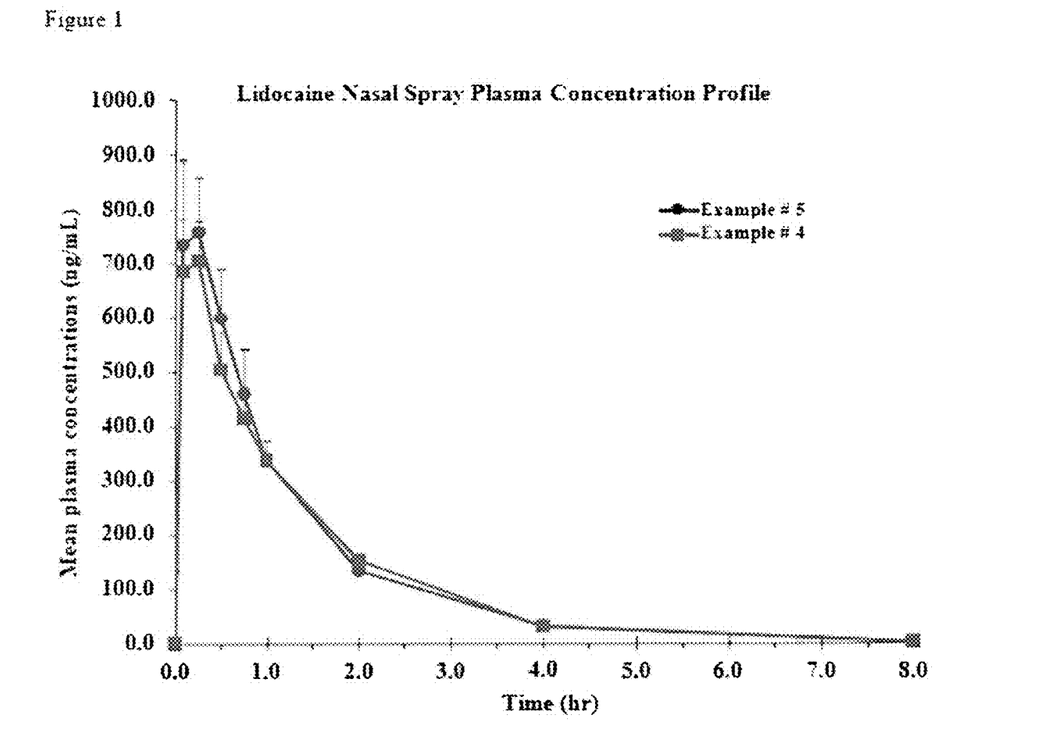
FIG. 1 is a graph depicting the mean pharmacokinetics profile of the lidocaine intranasal spray of Examples 4 and 5.

The plasma concentration-time profile, individual and mean pharmacokinetic parameters of Lidocaine following Intranasal (Example 4 and 5) and Placebo route of administration are presented in Table 5. The mean pharmacokinetic (plasma concentration-time) profiles are represented in FIG. 1.

Lidocaine plasma concentrations were found below LLOQ for placebo group #3 and were not considered for estimation of PK parameters.

Group 1 (Example 5

The mean Cmax was found to be 724 ng/mL at median Tmax of 0.25 hr. The mean $AUC_{0-t}$ and $AUC_{0-infinity}$ was found to be 964 and 993 ng*hr/ml, respectively. The mean elimination half-life was found to be 0.998 hr. The clearance and volume of distribution were 345 ml/min and 29.2 L, respectively.

Group 1 (Example 4

The mean Cmax was found to be 808 ng/mL at median Tmax of 0.25 hr. The $AUC_{0-t}$ and $AUC_{0-infinity}$ was found to be 979 and 1010 ng*hr/ml, respectively. The mean elimination half-life was found to be 0.928 hr. The clearance and volume of distribution were 345 ml/min and 27 L, respectively.

TABLE 5

| | Group/Formulation | |
|---|---|---|
| | Group 1 Example # 5 | Group 2 Example # 4 |
| | Dose/ROA | |
| PK Parameters | 20 mg/rabbit, Intranasal Spray | 20 mg/rabbit, Intranasal Spray |
| $C_{max}$ (ng/mL) | 724 ± 112 (15.4) | 808 ± 198 (24.5) |
| $T_{max}$ (hr) [a] | 0.25 (0.08-0.25) | 0.25 (0.08-0.25) |
| $AUC_{0-t\ hr}$ (ng*hr/mL) | 964 ± 172 (17.9) | 979 ± 225 (23) |
| $AUC_{0-infinity}$ (ng*hr/mL) | 993 ± 166 (16.6) | 1010 ± 224 (22.2) |
| Kel (1/hr) | 0.728 + 0.173 (23.8) | 0.772 ± 0.137 (17.8) |

TABLE 5-continued

| | Group/Formulation | |
|---|---|---|
| | Group 1 Example # 5 | Group 2 Example # 4 |
| | Dose/ROA | |
| PK Parameters | 20 mg/rabbit, Intranasal Spray | 20 mg/rabbit, Intranasal Spray |
| $t_{1/2}$ (hr) | 0.998 ± 0.237 (23.8) | 0.928 ± 0.203 (21.8) |
| CL/F (mL/min) | 345 ± 64.3 (18.6) | 345 ± 79.1 (23) |
| $V_Z$/F (L) | 29.2 ± 5.36 (18.4) | 27 ± 4.34 (16.1) |

*N = 6 (3 males + 3 females)

Note:
Values are Mean ± SD (% CV);

[a] represents Median (minimum-maximum); ROA = Route of administration; CV = Coefficient of variation.
As group 3 was treated with test formulation 3 (placebo), no plasma concentrations of Lidocaine were observed.

Formalin Irritation Study

Figure 2:
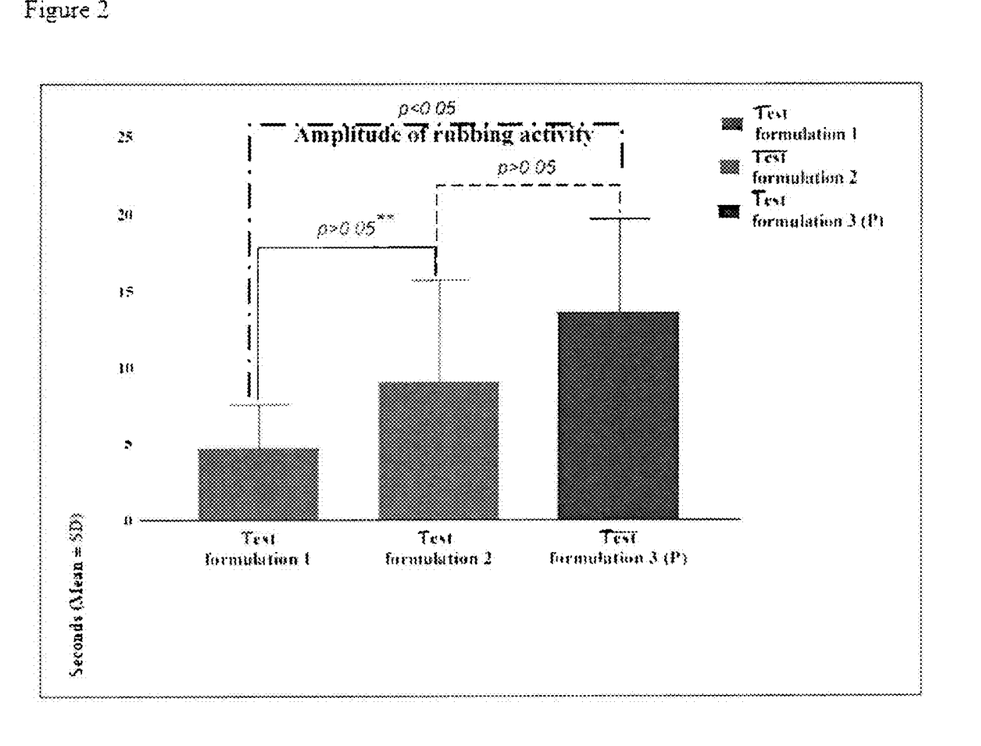
FIG. 2 is a graph the amplitude of rubbing activity at a formalin injected site for 45 minutes post-dose of formalin in test formulations of Examples 4 and 5 versus placebo in treated rabbits.

The total amplitude of the measured behavior (total time spent in rubbing of the formalin injected site) were found to be 27.91, 53.78 and 81.83 seconds for test formulation Example #5, Example #4 and placebo respectively. Mean amplitude were found to be 4.65, 8.96 and 13.64 seconds for the test formulations of Example 5 (identified as test formulation 1 in FIG. 2), Example 4 (identified as test formulation 2 in FIG. 2) and placebo (identified as test formulation 3 in FIG. 2), respectively. The data was analyzed statistically using unpaired t-test for comparison of test formulation Example 4 and Example 5 with placebo formulation. The amplitude of rubbing activity was given in FIG. 2. The significant reduction in formalin induced pain/irritation score was observed in both the test formulation Example 4 and Example 5 when compared with the placebo formulation.

Example 10 (Stability Data

In Example 10, 5 ml glass bottles were filled with the formulation of Example 4 (base) and Example 5 (hydrochloride salt) with a metered dose spray pump and subjected to stability under following conditions:
  ICH accelerated conditions (ACC) at 40° C.±2° C./75% RH±5% RH; and
  ICH room temperature conditions (CRT) at 25° C.±2° C./60% RH±5% RH.

The International Council for Harmonization of Technical Requirements for Pharmaceuticals for Human Use ("ICH") is a project that brings together the regulatory authorities of Europe, Japan and the United States and experts from the pharmaceutical industry.

Samples were analyzed to measure the Lidocaine assay, impurities and physical stability (drug precipitation, color change and PH). The stability data is provided in Tables 6 and 7 below.

TABLE 6

Stability data of Example 4 (Lidocaine base)

| | | | 40° C. ± 2° C./ 75% RH ± 5% RH | | | 25° C. ± 2° C./ 60% RH ± 5% RH | | |
|---|---|---|---|---|---|---|---|---|
| Test | Specification | Initial | 1 M | 3 M | 6 M | 6 M | 12 M | 24 M |
| Physical Appearance | Complies | Y | Y | Y | Y | Y | Y | Y |
| Assay by HPLC | 90.0-110.0% | 99.0% | 100.4% | 98.2% | 94.0% | 98.3% | 96.9% | 94.8% |
| Total Impurities | NMT 2.0% | ND | ND | ND | ND | ND | ND | 0.2 |

Y—Complies
ND—Not detected

TABLE 7

Stability data of Example 5 (Lidocaine Hydrochloride)

| | | | 40° C. ± 2° C./ 75% RH ± 5% RH | | | 25° C. ± 2° C./ 60% RH ± 5% RH | | |
|---|---|---|---|---|---|---|---|---|
| Test | Specification | Initial | 1 M | 3 M | 6 M | 6 M | 12 M | 24 M |
| Physical Appearance | Complies | Y | Y | Y | Y | Y | Y | Y |
| Assay by | 90.0-110.0% | 99.6% | 100.2% | 99.0% | 94.7% | 96.1% | 98.4% | 100.7% |

TABLE 7-continued

Stability data of Example 5 (Lidocaine Hydrochloride)

| Test | Specification | Initial | 40° C. ± 2° C./ 75% RH ± 5% RH | | | 25° C. ± 2° C./ 60% RH ± 5% RH | | |
|---|---|---|---|---|---|---|---|---|
| | | | 1 M | 3 M | 6 M | 6 M | 12 M | 24 M |
| HPLC Total Impurities | NMT 2.0% | ND | ND | ND | ND | ND | ND | ND |

Y—Complies
ND—Not detected

CONCLUSION

The examples provided above are not meant to be exclusive. Many other variations of the present invention would be obvious to those skilled in the art, and are contemplated to be within the scope of the appended claims.

The active agents may be incorporated into the intranasal formulations in therapeutically equivalent amounts. The actual dose of an active agent (relative potency) may be determined based on a comparative dose to a therapeutically effective dose of an active agent described herein.

The invention claimed is:

1. A method of treating pain associated with a condition selected from the group consisting of tri-geminal neuralgia, facial neuropathic pain, facial cancer induced neuropathic pain, migraine pain, and cluster headache pain, comprising incorporating a preservative-free nasal spray formulation into a mechanical multi-dose nasal spray pump device, the nasal spray formulation consisting of from about 5% to about 30% w/v of a locally active sodium channel blocker or a pharmaceutically acceptable salt thereof, from about 0.25% to about 5% w/v of a buffering agent, an optional second active agent selected from the group consisting of epinephrine, ketamine, a vasodilator, an anticonvulsant drug, a muscle relaxant, and combinations of any of the foregoing, and from about 5 to about 99% w/v of a pharmaceutically acceptable carrier for nasal administration, the nasal spray formulation having a viscosity from about 0.8 to about 1.1 cps, the mechanical multi-dose nasal spray pump device spraying a unit dose of the nasal spray formulation in a wide plume to provide a mean spray angle from about 50 to about 95 degrees and small droplet size having a mean Dv 10 from about 10 to about 30 µm, a mean Dv50 from about 20 to about 60 µm, and a mean Dv90 from about 80 to about 120 µm when actuated, the unit dose when sprayed into the nasal cavity of a human patient being therapeutically effective to treat a condition selected from the group consisting of tri-geminal neuralgia, facial neuropathic pain, facial cancer induced neuropathic pain, migraine pain, and cluster headache pain.

2. The method of claim 1, wherein the locally active sodium channel blocker is a local anesthetic selected from the group consisting of lidocaine, bupivacaine, ropivacaine, mepivacaine, tetracaine, pharmaceutically acceptable salts thereof, and mixtures of any of the foregoing.

3. The method of claim 2, wherein the mechanical multi-dose nasal spray pump device provides a volume of about 0.04 ml to about 0.2 ml and the locally active sodium channel blocker is supersaturated in the formulation.

4. The method of claim 1, wherein the locally active sodium channel blocker is lidocaine and a unit dose of the nasal spray formulation provides from about 5 mg to about 20 mg lidocaine or a pharmaceutically acceptable salts thereof sprayed into the nasal cavity of the human subject, further comprising administering the nasal spray formulation at about 4 hour intervals.

5. The method of claim 4, further comprising intranasally administering the nasal spray formulation by actuating the mechanical multi-dose nasal spray pump device and spraying 1-2 sprays in each nostril of a human subject in every application to provide an effective dose of the locally active sodium channel blocker.

6. The method of claim 5, further comprising incorporating the second active agent into the nasal spray formulation.

7. The method of claim 1, wherein the mean spray angle is from about 60 to about 90 degrees.

8. The method of claim 1, further comprising providing the mechanical multi-dose nasal spray pump device such that the device when activated provides a mean plume width (mm) from about 20 to about 70 mm.

9. The method of claim 8, wherein the mean plume width is from about 30 to about 60 mm.

10. The method of claim 1, wherein the mechanical multi-dose nasal spray pump device provides a mean spray angle from about 50 to about 95 degrees.

11. The method of claim 1, wherein the spray pattern of the mechanical multi dose nasal spray pump device provides a mean $D_{min}$ from about 15 to about 45 mm, a $D_{max}$ from about 40 to about 70 mm, and an ovality ratio from about 0.5 to about 2 mm.

12. The method of claim 1, wherein the pharmaceutically acceptable carrier for nasal administration comprises water.

13. The method of claim 1, further comprising arranging the mechanical multi-dose spray pump device such that when actuated, it provides a spray droplet size from about 5 to about 500 microns.

14. The method of claim 1, wherein the nasal spray formulation is preservative-free and includes a locally acting sodium channel blocker comprising lidocaine or a pharmaceutically acceptable salt thereof, and a second active agent selected from the group consisting of a vasodilator, an anticonvulsant drug, a muscle relaxant, epinephrine, ketamine, and mixtures of any of the foregoing.

15. A method of treating pain associated with a condition selected from the group consisting of tri-geminal neuralgia, facial neuropathic pain, facial cancer induced neuropathic pain, migraine pain, and cluster headache pain, comprising incorporating a preservative-free nasal spray formulation into a mechanical multi-dose nasal spray pump device, the nasal spray formulation consisting of from about 5% to about 30% w/v of a locally acting sodium channel blocker selected from the group consisting of lidocaine, mepivacaine, bupivacaine, ropivacaine, chloroprocaine, procaine, tetracaine, a pharmaceutically acceptable salt thereof, and any combination of the foregoing to treat pain, from about 0.25% to about 5% w/v of a buffering agent, the buffering agent being in a sufficient amount to provide a pH of the nasal spray formulation from about pH 4.5 to about pH 7, an optional second active agent selected from the group consisting of epinephrine, ketamine, a vasodilator, an anticonvulsant drug, a muscle relaxant, and combinations of any of the foregoing, and from about 5 to about 99% w/v of a pharmaceutically acceptable carrier for nasal administration, the nasal spray formulation having a viscosity from about 0.8 to about 1.1 cps, and intranasally administering the nasal spray formulation by actuating the mechanical multi-dose nasal spray pump device and spraying 1-2 sprays in each nostril of a human subject, for a total of 4 sprays in every application, the mechanical multi-dose nasal spray pump device spraying a unit dose of the nasal spray formulation in a wide plume such that the spray pump pattern has a mean spray angle from about 60 to about 90 degrees, and droplet size when actuated such that the mean Dv10 is from about 10 to about 30 μm, the mean Dv50 is from about 20 to about 60 μm, and the mean Dv90 is from about 80 to about 120 μm, the unit dose when sprayed into the nasal cavity of a human patient being therapeutically effective to treat a condition selected from the group consisting of tri-geminal neuralgia, facial neuropathic pain, facial cancer induced neuropathic pain, migraine pain, and cluster headache pain, wherein the mechanical multi-dose nasal spray pump device when actuated provides a volume of about 0.04 ml to about 0.2 ml.

16. The method of claim 15, wherein spray pattern of the multi-dose pump spray provides a mean $D_{min}$ from about 15 to about 45 mm, a $D_{max}$ from about 40 to about 70 mm, an ovality ratio from about 0.5 to about 2 mm, and a % area from about 12 to about 22 mm.

17. The method of claim 15, wherein the locally acting sodium channel blocker is lidocaine or a pharmaceutically acceptable salt thereof, and a unit dose of the nasal spray formulation provides from about 5 mg to about 20 mg lidocaine or a pharmaceutically acceptable salt thereof sprayed into the nasal cavity of the human subject.

18. The method of claim 15, wherein the nasal spray formulation includes the second active agent.

19. The method of claim 15, wherein the nasal spray formulation is preservative-free and includes a locally acting sodium channel blocker comprising lidocaine or a pharmaceutically acceptable salt thereof.

* * * * *